(12) United States Patent
Miller

(10) Patent No.: US 7,101,336 B2
(45) Date of Patent: Sep. 5, 2006

(54) METHODS AND SYSTEMS FOR MOTION ADAPTIVE SPATIAL COMPOUNDING

(75) Inventor: Steven Charles Miller, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 281 days.

(21) Appl. No.: 10/722,003

(22) Filed: Nov. 25, 2003

(65) Prior Publication Data

US 2005/0113696 A1 May 26, 2005

(51) Int. Cl.
*A61B 8/00* (2006.01)
(52) U.S. Cl. .................................. 600/443
(58) Field of Classification Search ........ 600/440–441, 600/443, 447, 454–456, 458; 128/916
See application file for complete search history.

(56) References Cited

U.S. PATENT DOCUMENTS

| | | | |
|---|---|---|---|
| 4,159,462 A | 6/1979 | Rocha et al. | |
| 4,319,489 A | 3/1982 | Yamaguchi et al. | |
| 4,418,575 A | 12/1983 | Hundt et al. | |
| 4,649,927 A | 3/1987 | Fehr et al. | |
| 5,127,409 A | 7/1992 | Daigle | |
| 5,529,070 A | 6/1996 | Augustine et al. | |
| 5,566,674 A * | 10/1996 | Weng | 600/443 |
| 5,782,766 A | 7/1998 | Weng et al. | |
| 5,908,390 A | 6/1999 | Matsushima | |
| 6,117,081 A | 9/2000 | Jago et al. | |
| 6,126,598 A | 10/2000 | Entrekin et al. | |
| 6,126,599 A | 10/2000 | Jago et al. | |
| 6,135,956 A | 10/2000 | Schmiesing et al. | |
| 6,210,328 B1 | 4/2001 | Robinson et al. | |
| 6,224,552 B1 | 5/2001 | Jago et al. | |
| 6,283,917 B1 | 9/2001 | Jago et al. | |
| 6,331,116 B1 | 12/2001 | Kaufman et al. | |
| 6,416,477 B1 | 7/2002 | Jago | |
| 6,423,004 B1 | 7/2002 | Dong et al. | |
| 6,527,720 B1 | 3/2003 | Ustuner et al. | |
| 6,530,885 B1 | 3/2003 | Entrekin et al. | |
| 6,542,626 B1 | 4/2003 | Brouwer et al. | |
| 6,544,177 B1 | 4/2003 | Robinson | |
| 6,547,732 B1 | 4/2003 | Jago | |
| 6,551,246 B1 | 4/2003 | Ustuner et al. | |
| 6,572,549 B1 | 6/2003 | Jong et al. | |
| 6,641,536 B1 * | 11/2003 | Hossack et al. | 600/443 |
| 6,872,181 B1 * | 3/2005 | Tirumalai et al. | 600/447 |
| 2003/0092989 A1 | 5/2003 | Aichhorn et al. | |
| 2005/0075569 A1* | 4/2005 | Li et al. | 600/454 |

* cited by examiner

*Primary Examiner*—Francis J. Jaworski
(74) *Attorney, Agent, or Firm*—Small Patent Law Group; Dean D. Small

(57) ABSTRACT

A method of medical ultrasound imaging is provided. The method includes transmitting ultrasound waves into a volume at a first rate, receiving ultrasound echoes for each of the ultrasound waves, each echo is indicative of a density interface within the volume, each set of received echoes that corresponds to a single transmitted wave defines a steering frame, detecting motion of the array transducer, and combining a plurality of steering frames into a compound image based on the detected array transducer motion.

31 Claims, 3 Drawing Sheets

METHODS AND SYSTEMS FOR MOTION ADAPTIVE SPATIAL COMPOUNDING

BACKGROUND OF THE INVENTION

The present invention relates to diagnostic ultrasound systems. In particular, the present invention relates to methods and apparatus for acquiring and processing ultrasound data to reduce blurring of ultrasound images.

At least some known ultrasound systems are capable of spatially compounding a plurality of ultrasound images of a given target into a compound image. The term "compounding" as used throughout means combining multiple data sets non-coherently to create a new, single data set. The plurality of data sets may each be obtained from a different steering angle and/or aperture and/or may each be obtained at a different time. The plurality of data sets or steering frames are combined to generate a single view or compound image by combining the data received from each point in the compound image target which has been received from each steering angle or aperture. Real time spatial compound imaging may be performed by acquiring a series of partially overlapping component image frames from substantially independent steering angles. An array transducer may be utilized to implement electronic beam steering and/or electronic translation of the component frames. The component frames are combined into a compound image by summation, averaging, peak detection, or other combinational means. The compounded image may display relatively lower speckle and better specular reflector delineation than a non-spatially compounded ultrasound image from a single angle.

In real time spatial compound imaging, several image acquisitions are needed to produce each new compound image frame. A time difference exists between acquisition of the first steering frame used in constructing the compound image and the last steering frame used in the image. Significant image misregistration may exist due to the time difference between the acquisition of frames. The image misregistration may result in compound image blurring if a large number of steering frames are used to construct the compound image. Relatively less blurring may result if a smaller number of steering frames are used to construct the image. As discussed above, it is generally desirable to acquire a large number of steering frames to maximize the image quality of the compound image. However, a large number of steering frames requires a longer period of time for acquisition, during which blurring may increase to an undesirable level, especially when the array transducer is in motion.

BRIEF DESCRIPTION OF THE INVENTION

In one embodiment, a method of medical ultrasound imaging is provided. The method includes transmitting ultrasound waves into a volume at a first rate and receiving ultrasound echoes for each of the ultrasound waves. Each echo is indicative of a density interface within the volume. Each set of received echoes that corresponds to a single transmitted wave defines a steering frame. The method further includes detecting motion of the array transducer, and combining a plurality of steering frames into a compound image based on the detected array transducer motion.

In another embodiment, an ultrasound system is provided that includes an array transducer transmitting and receiving ultrasound signals, a transmitter for transmitting signals to the transducer wherein the transducer transmits ultrasound waves into a volume at different steering angles and a receiver for receiving signals from the transducer that is indicative of ultrasound echoes for each of the ultrasound waves. Each echo is indicative of a density interface within the volume, and each set of received echoes that corresponds to a single transmitted wave defines a steering frame. The system further includes a signal processor detecting motion of the array transducer and combining steering frames into a compound image based on the detected array transducer motion, and a display for outputting information based on the compound images.

In yet another embodiment, a computer program embodied on a computer readable medium for controlling medical ultrasound imaging is provided. The program includes a code segment that transmits a plurality of ultrasound waves into a volume at a first rate and receives ultrasound echoes for each of the ultrasound waves. Each received echo is indicative of a density interface within the volume. Each set of received echoes that corresponds to a single transmitted wave defines a steering frame. The computer program further includes detecting motion of the array transducer, and combining a plurality of steering frames into a compound image based on the detected array transducer motion.

DETAILED DESCRIPTION OF THE INVENTION

Figure 1:
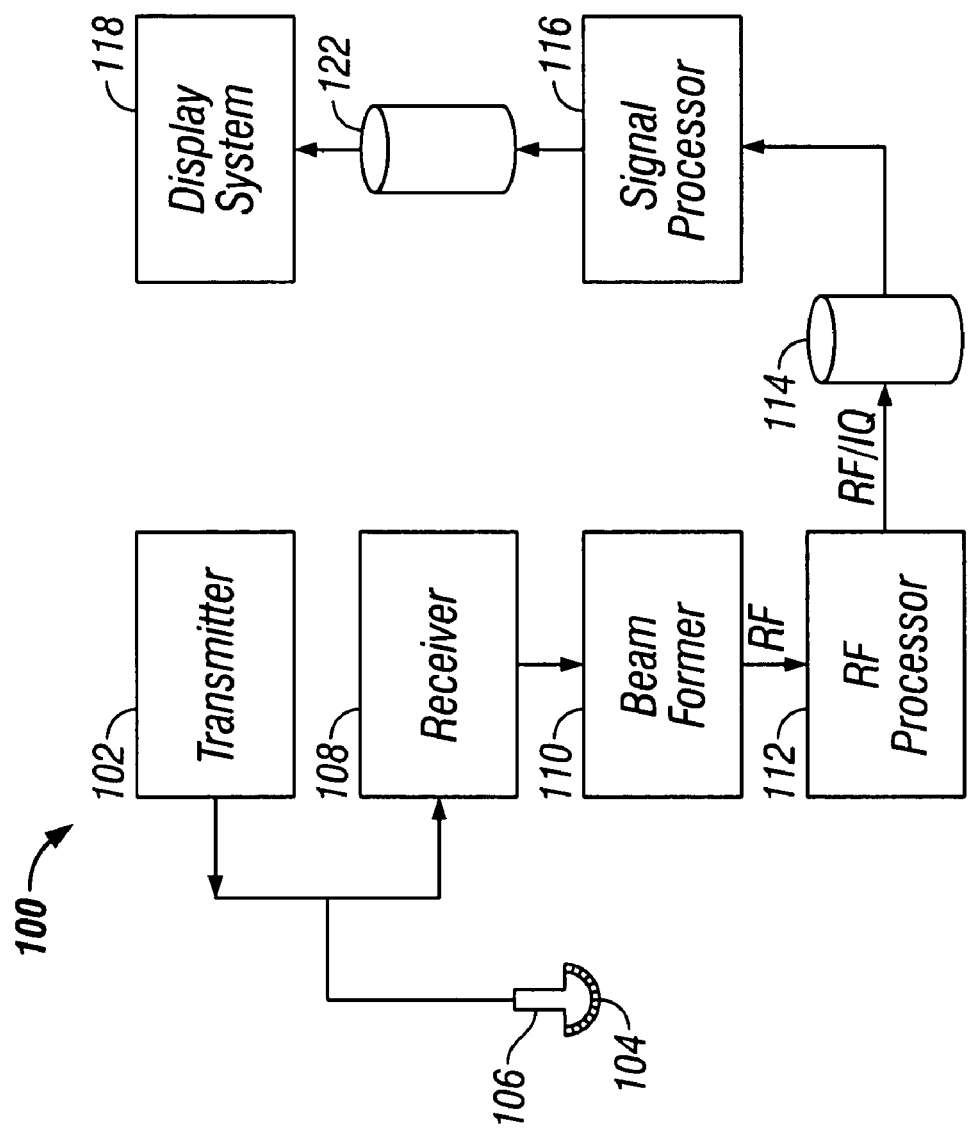
FIG. 1 is a block diagram of an ultrasound system formed in accordance with an embodiment of the present invention.

FIG. 1 is a block diagram of an ultrasound system 100 formed in accordance with an embodiment of the present invention. Ultrasound system 100 includes a transmitter 102 that drives a plurality of transducer elements 104 within an array transducer 106 to emit pulsed ultrasound signals into a body. A variety of geometries may be used. The ultrasound signals are back-scattered from density interfaces and/or structures in the body, like blood cells or muscular tissue, to produce echoes which return to transducer elements 104. A receiver 108 receives the echoes. The received echoes are passed through a beamformer 110, which performs beamforming and outputs a RF signal. The RF signal then passes through a RF processor 112. Alternatively, RF processor 112 may include a complex demodulator (not shown) that demodulates the RF signal to form IQ data pairs representative of the echo signals. The RF or IQ signal data may then be routed directly to RF/IQ buffer 114 for temporary storage.

Ultrasound system 100 also includes a signal processor 116 to process the acquired ultrasound information (i.e., RF signal data or IQ data pairs) and prepare frames of ultrasound information for display on display system 118. Signal processor 116 is adapted to perform one or more processing operations according to a plurality of selectable ultrasound modalities on the acquired ultrasound information. In the exemplary embodiment, acquired ultrasound information is processed in real-time during a scanning session as the echo signals are received. In an alternative embodiment, the ultrasound information may be stored temporarily in RF/IQ buffer 114 during a scanning session and processed in less than real-time in a live or off-line operation.

Ultrasound system 100 may continuously acquire ultrasound information at a frame rate that exceeds fifty frames per second, which is approximately the perception rate of the human eye. The acquired ultrasound information may be displayed on display system 118 at a slower frame-rate. An image buffer 122 is included for storing processed frames of acquired ultrasound information that are not scheduled to be displayed immediately. In the exemplary embodiment, image buffer 122 is of sufficient capacity to store at least several seconds worth of frames of ultrasound information. The frames of ultrasound information are stored in a manner to facilitate retrieval thereof according to its order or time of acquisition. Image buffer 122 may include at least one memory device, such as, but not limited to, a read only memory (ROM), a flash memory, and/or a random access memory (RAM) or other known data storage medium.

Figure 2:
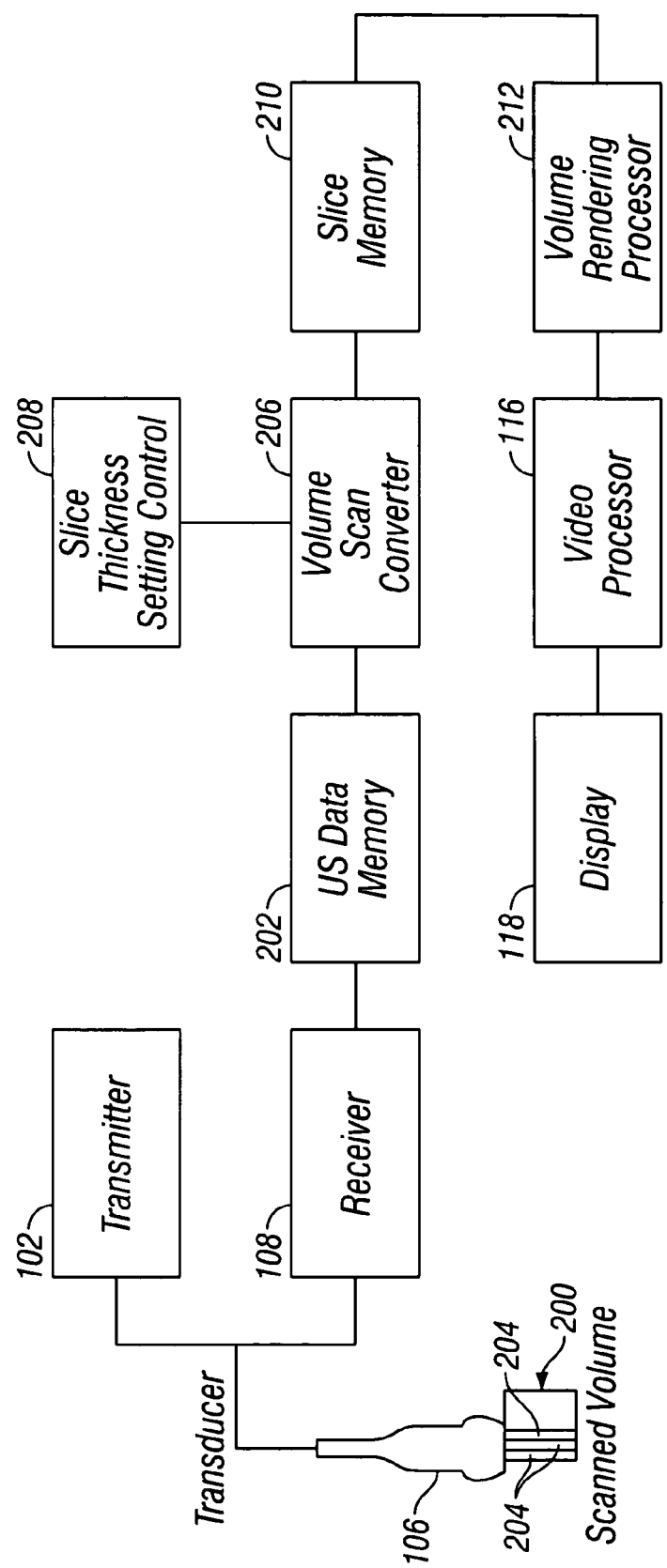
FIG. 2 is another block diagram of an ultrasound system used to acquire and process ultrasound images formed in accordance with an embodiment of the present invention.

FIG. 2 is another block diagram of the exemplary ultrasound system 100 (shown in FIG. 1) that may be used to acquire and process ultrasound images. System 100 includes array transducer 106 connected to transmitter 102 and a receiver 108. Array transducer 106 transmits ultrasound pulses and receives echoes from structures inside of a scanned ultrasound volume 200. A memory 202 stores ultrasound data from receiver 108 derived from scanned ultrasound volume 200. Volume 200 may be obtained by various techniques, for example, but not limited to, 3D scanning, real-time 3D imaging, volume scanning, 2D scanning with transducers having positioning sensors, freehand scanning using a Voxel correlation technique, 2D or matrix array transducers.

Transducer 106 may be moved, such as along a linear or arcuate path, while scanning a region of interest (ROI). At each linear or arcuate position, transducer 106 obtains a plurality of scan planes 204. Scan planes 204 may be collected for a thickness, such as from a group or set of adjacent scan planes 204. Scan planes 204 are stored in memory 202, and then passed to a volume scan converter 206. In some embodiments, transducer 106 may obtain lines instead of scan planes 204, and memory 202 may store lines obtained by transducer 106 rather than scan planes 204. Volume scan converter 206 may store lines obtained by transducer 106 rather than scan planes 204. Volume scan converter 206 receives a slice thickness setting from a control input 208, which identifies the thickness of a slice to be created from scan planes 204. Volume scan converter 206 creates a data slice from multiple adjacent scan planes 204. The number of adjacent scan planes 204 that are obtained to form each data slice is dependent upon the thickness selected by slice thickness control input 208. The data slice is stored in a slice memory 210 and is accessed by a volume rendering processor 212. Volume rendering processor 212 performs volume rendering upon the data slice. The output of volume rendering processor 212 is passed to video processor 116 and display 118.

Figure 3:
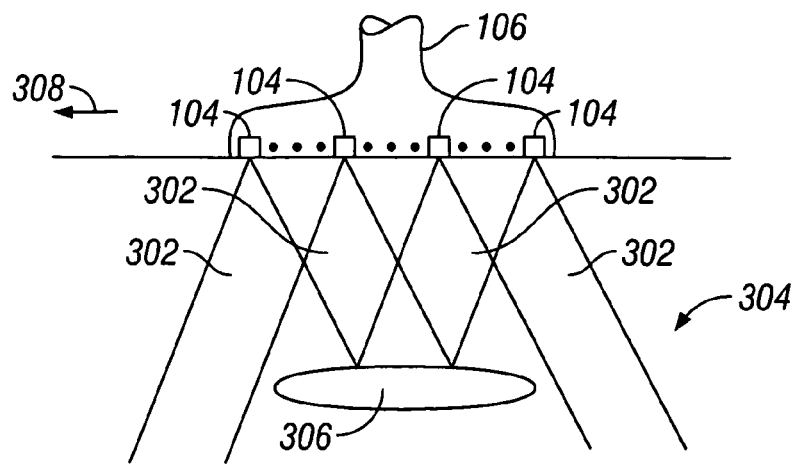
FIG. 3 illustrates an exemplary display of an object acquired by the ultrasound system shown in FIG. 1.

FIG. 3 illustrates an exemplary display 300 of an object acquired by system 100 (shown in FIG. 1). Array transducer 106 includes a plurality of transducer elements 104 positioned linearly along an edge of transducer 106. Transducer elements 104 are coupled to transmitter 102 and receiver 108 (shown in FIG. 1) and are responsive to transmit signals from transmitter 102 to generate an ultrasound beam or wave 302 that emanates from the edge of array transducer 106 proximate each transducer element 104. The transmit signals may be phased to control the firing of each transducer element 104 to steer ultrasound wave 302 along a predetermined path. For illustration purposes only, four transducer elements 104 are illustrated. Array transducer 106 may include any number of transducer elements 104. Each wave 302 is projected into a volume of interest 304 that may contain an object of interest 306 and may overlap one or more of waves 302 emanating from adjacent transducer elements 104. Object 306 may absorb, transmit, refract and/or reflect waves 302 that impact object 306. Reflected waves or echoes from object 306 are received by transducer elements 104 and processed by system 100 to create image or steering frames indicative of the object 306 and other objects within volume 304.

A predetermined number of image frames are then combined into a compound image by system 100. The compound image may include frames representative of views of object 306 from different angles enabled by the spatial separation of transducer elements 104 along array transducer 106. Errors in angle due to refraction may cause misregistration between frames that view object 306 from different angles. Misregistration between the image frames may also occur due to motion 308 of array transducer 106 during the transmit and receive process. Image frames may be separated from each other in time as well as spatially.

Registration algorithms that make use of geometrical features in the images such as points, lines and surfaces, determine the transformation by identifying features such as sets of image points that correspond to the same physical entity visible in both frames. Registration algorithms may be based on image intensity values such that they determine an image transformation that optimizes a similarity measure between each frame.

Misregistration between steering frames can be measured by a number of motion tracking methods such as a correlation block search, Doppler tissue velocity, accelerometers or other motion sensors, and feature tracking. The degree of misregistration may also be detected by a cross correlation method. Alternatively, motion 308 of array transducer 106 may also be detected by comparing the information of compounded images. Operating the ultrasound system in various modes is selectable by the user. In the exemplary embodiment, system 100 will determine an optimum number of frames to be used in constructing the compounded image automatically and continuously. In an alternative embodiment, the user may select the number of frames used to construct the compound image manually.

Misregistration between component frames can be measured by a number of motion tracking methods such as correlation block search wherein consecutive ultrasound image frames are correlated in order to derive transducer motion information. The individual images may then be divided into several smaller sub-image regions and an image motion detection algorithm may be used to measure the sub-image motion and then to determine an estimation of the local motion. The initial estimation is combined with measurement parameters to derive a final estimation of the local motion. The final local motion then may be used to estimate global image motion. A compounded image may be then displayed based on the derived global image motion. Using Doppler tissue velocity ultrasound system 100 may track the velocity and position of array transducer 106 by making use of a pair of range points that are located at predetermined positions along a scan line to facilitate determining misregistration. Also accelerometers or other motion sensors and feature tracking may be used to detect misregistration. However, these methods generally require large amounts of computation. The effect of misregistration can be detected without explicit measurement of the motion by comparing the similarity or difference of one component frame with a subsequent frame in the temporal sequence. Similarity or difference metrics such as cross correlation wherein one image representation is multiplied by successively time-shifted versions of a successive image representation to quantify movement of array transducer 106, or a sum of absolute differences method wherein, generally require less computation than motion estimation, and can be used to quantify frame-to-frame similarity or difference in at least one region of interest within the frame.

Detecting a rate of change of misregistration between frames making up a compounded image may be used to further adjust the number of frames used in constructing the compound image. A rate of change of misregistration between frames making up a compounded image correlates to a rate of change of motion of array transducer 106. Specifically, if the rate of change of motion of array transducer 106 is large, greater misregistration between image frames may be expected. In order to counter the effects of large image misregistration, system 100 may reduce the number of image frames used to construct a compound image to a lesser number of image frames that are used when the rate of change of motion is less. Additionally, system 100 may reduce the time elapsed before reducing the number of image frames used to construct a compound image to a lesser amount of time than is used when the rate of change of motion is less.

In operation, system 100 may use a first number of frame images to construct a compound image, such as, twenty-four, when array transducer 106 is maintained substantially stationary with respect to the body being scanned. If array transducer 106 is placed into motion 308 with respect to the body, system 100 detects the motion 308 and the rate of change of the motion of array transducer 106. If motion 308 of array transducer 106 exceeds a predetermined value, system 100 may modify the number of image frames used to construct a compound image to reduce the effects of motion 308. System 100 may incorporate a delay, such that the number of frames used to construct the compound image is not modified immediately upon array transducer 106 exceeding the predetermined value. The delay may be useful to maintain display image stability during periods when array transducer 106 may be moved a relatively short distance or for a relatively short period of time. It may be the case though, that rapid motion of array transducer 106 may be detrimental to display image stability. For example, a relatively large increase the rate of change of motion of transducer 106 may indicate the misregistration of the upcoming image frames will be large, such that a compound image constructed from the current number of image frames may be unusable due to poor image stability. Based on the rate of change of motion of array transducer 106, system 100 may modify the number of frame images used to construct a compound image to a second number of frame images that facilitates maintaining stability of the displayed image and system 100 may modify the time delay used between when the rate of change of motion of array transducer 106 is detected to be exceeding a predetermined value and when system 100 modifies the number of frame images used to construct the compound image.

Figure 4:
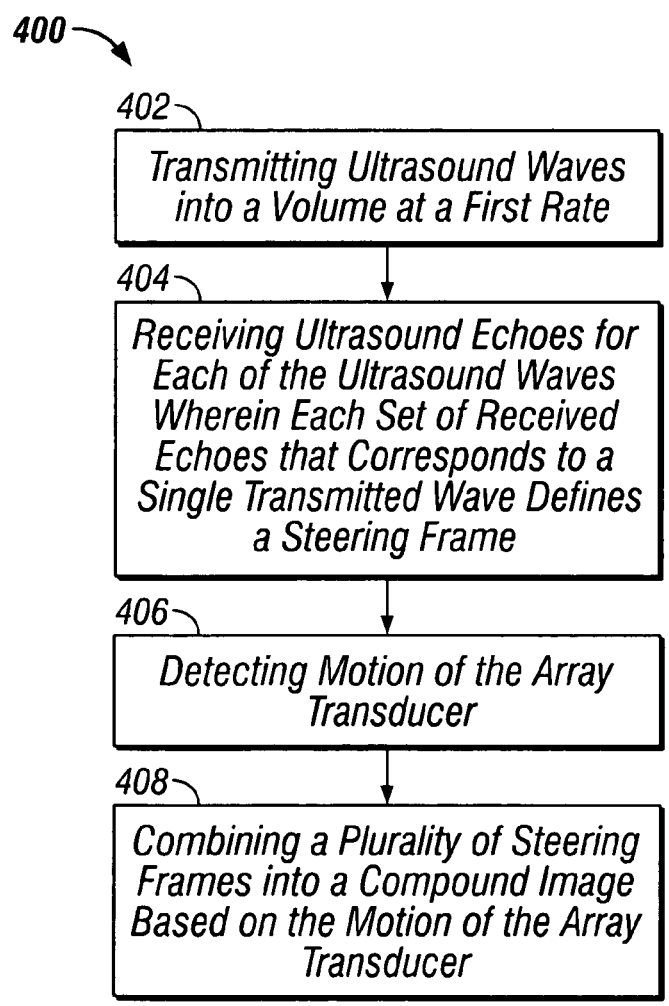
FIG. 4 is a block diagram of an exemplary method for acquiring and processing images using the ultrasound system shown in FIG. 1 and formed in accordance with an embodiment of the present invention.

FIG. 4 is a block diagram of an exemplary method 400 for acquiring and processing images using system 100 (shown in FIG. 1). Method 400 includes transmitting 402 ultrasound waves into a volume at a first rate. In the exemplary embodiment, he volume is a living body. In alternative embodiments, the volume may include any object that may yield desirable information through ultrasound interrogation. Array transducer 106 transmits 402 ultrasound beams at different angles over an image field denoted by scanlines (shown in FIG. 3). Each beam being steered at a different angle relative to array transducer 106. The transmission of the beams is controlled by a transmitter 102 which controls the phasing and time of actuation of each of the elements of the array transducer so as to transmit each beam from a predetermined origin along the array and at a predetermined angle.

Method 400 includes receiving 404 ultrasound echoes for each of the ultrasound waves in the beams, each echo is indicative of a density interface within the volume, each set of received echoes that corresponds to a single transmitted wave defines a steering frame. The echoes returned from along each scanline are received by transducer elements 104 in array transducer 106, digitized by, for example, analog to digital conversion, and coupled to a digital beamformer 110. The digital beamformer delays and sums the echoes from the array elements to form a sequence of focused, coherent digital echo samples along each scanline. Transmitter 102 and beamformer 110 are operated under control of a system controller (not shown). The system controller provides an interface to control settings, which may be set by a user. The system controller controls the transmitter to transmit the desired number of scanline groups at the desired angles, transmit energies and frequencies. The system controller also controls the digital beamformer to properly delay and combine the received echo signals for the apertures and image depths used.

System 100 detects 406 motion of array transducer 106 and also detects a rate of change of motion of array transducer 106. The motion and rate of change of motion signals are compared to predetermined limit values to modify the image process of system 100. Specifically, the motion of array transducer 106 may be used to determine a number of image frames that is used in constructing a compound image. The rate of change of motion of array transducer 106 may be used to determine a delay period before the number of image frames used to construct the compound image is modified based on motion of array transducer 106. Additionally, the rate of change of motion of array transducer 106 may be used to determine the number of image frames used to construct the compound image directly. After the motion of array transducer 106 is determined system 100 combines 408 a plurality of steering frames into a compound image based on the detected motion and rate of change of motion of array transducer 106.

The above-described motion adaptive image compounding method is cost-effective and highly reliable for modifying image-compounding operation of a spatially compounded ultrasound imaging system. Specifically, the motion adaptive image compounding method facilitates combining ultrasound image frames such that motion of the array transducer causes the frame compounding to be modified to facilitate maintaining display image stability. As a result, the methods and apparatus described herein facilitate ultrasound imaging in a cost-effective and reliable manner.

Exemplary embodiments of diagnostic ultrasound systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method of medical ultrasound imaging using a medical ultrasound imaging system that includes an array transducer, said method comprising:
   transmitting ultrasound waves into a volume at a first rate;
   receiving ultrasound echoes for each of the ultrasound waves wherein each set of received echoes that corresponds to a single transmitted wave defines a steering frame;
   detecting motion of the array transducer;
   combining a plurality of steering frames into a compound image based on the motion of the array transducer; and
   determining, based on the motion of the array transducer, a delay period used before modifying a number of steering frames used to construct the compound image.

2. A method in accordance with claim 1 wherein detecting motion of the array transducer comprises detecting a rate of change of motion of the array transducer.

3. A method in accordance with claim 1 wherein detecting motion of the array transducer comprises detecting misregistration of successive steering frames due to motion of the array transducer.

4. A method in accordance with claim 3 wherein detecting misregistration of successive steering frames comprises detecting misregistration of successive steering frames due to a velocity of the array transducer.

5. A method in accordance with claim 3 wherein detecting misregistration of successive steering frames comprises detecting misregistration of successive steering frames using at least one of correlation block search, Doppler tissue velocity, an accelerometer, a motion sensor, feature tracking, cross correlation, and a sum of absolute differences.

6. A method in accordance with claim 3 wherein detecting misregistration of successive steering frames comprises detecting misregistration of successive steering frames using a compound image.

7. A method in accordance with claim 3 wherein combining a plurality of steering frames into a compound image comprises combining a first number of steering frames when a first level of misregistration is detected, and combining a second number of steering frames when a second level of misregistration is detected, the first number of steering frames being greater than the second number of steering frames, and wherein the second level of misregistration is associated with a greater level of array transducer motion than the first level of misregistration.

8. A method in accordance with claim 1 wherein combining a plurality of steering frames into a compound image comprises combining a plurality of steering frames into a compound image such that the number of steering frames combined is based on the detected array transducer motion.

9. A method in accordance with claim 1 wherein combining a plurality of steering frames into a compound image comprises combining a plurality of steering frames into a compound image using a weighted average of the steering frames such that a weighting on the broadside steered frame is proportional to the detected motion.

10. A method in accordance with claim 1 further comprising combining a plurality of steering frames into a compound image such that the number of steering frames combined is based on the detected array transducer motion using a compound image.

11. A method in accordance with claim 1 further comprising transmitting the plurality of ultrasound waves into the volume at a second rate based on the detected array transducer motion.

12. A medical ultrasound system, comprising: p1 an array transducer transmitting and receiving ultrasound signals for transmitting ultrasound waves into a volume at different steering angles;
   a receiver for receiving signals from said transducer indicative of ultrasound echoes for each of said ultrasound waves, each set of received echoes that corresponds to a single transmitted wave defining a steering frame;
   a signal processor detecting motion of the array transducer and combining said steering frames into a compound image based on the detected array transducer motion; and
   a display for outputting information based on said compound images, wherein said ultrasound system configured to determine, based on the motion of the array transducer, a delay period used before modifying a number of steering frames used to construct the compound image.

13. An ultrasound system in accordance with claim 12 wherein said signal processor is configured to detect misregistration of successive steering frames due to motion of the array transducer.

14. An ultrasound system in accordance with claim 13 wherein said signal processor is configured to detect misregistration of successive steering frames due to a velocity of the array transducer.

15. An ultrasound system in accordance with claim 13 wherein said signal processor is configured to detect misregistration of successive steering frames using at least one of correlation block search, Doppler tissue velocity, an accelerometer, a motion sensor, feature tracking, cross correlation, and a sum of absolute differences.

16. An ultrasound system in accordance with claim 13 wherein said signal processor is configured to detect misregistration of successive steering frames using a compound image.

17. An ultrasound system in accordance with claim 13 wherein said signal processor is configured to combine a first number of steering frames when a first level of misregistration is detected, and combine a second number of steering frames when a second level of misregistration is detected, the first number of steering frames being greater than the second number of steering frames, and wherein the second level of misregistration is associated with a greater level of array transducer motion than the first level of misregistration.

18. An ultrasound system in accordance with claim 12 wherein said signal processor is configured to combine a plurality of steering frames into a compound image such that the number of steering frames combined is based on the detected array transducer motion.

19. An ultrasound system in accordance with claim 12 wherein said signal processor is configured to combine a plurality of steering frames into a compound image using a weighted average of the steering frames such that a weighting on the broadside steered frame is proportional to the detected motion.

20. An ultrasound system in accordance with claim 12 wherein said signal processor is configured to combine a plurality of steering frames into a compound image such that the number of steering frames combined is based on the detected array transducer motion using a compound image.

21. An ultrasound system in accordance with claim 12 wherein said signal processor is configured to transmit the plurality of ultrasound waves into the volume at a second rate based on the detected array transducer motion.

22. A computer program embodied on a computer readable medium for controlling medical ultrasound imaging comprising a code segment that receives user selection input data and then:
- transmits ultrasound waves into a volume at different steering angles;
- receives ultrasound echoes for each of the ultrasound waves, each set of received echoes that corresponds to a single transmitted wave defining a steering frame;
- detects motion of the array transducer;
- combines a plurality of steering frames into a compound image based on the detected array transducer motion; and determines, based on the motion of the array transducer, a delay period used before modifying a number of steering frames used to construct the compound image.

23. A computer program in accordance with claim 22 further comprising a code segment that detects misregistration of successive steering frames due to motion of the array transducer.

24. A computer program in accordance with claim 23 further comprising a code segment that detects masregistration of successive steering frames due to a velocity of the array transducer.

25. A computer program in accordance with claim 23 further comprising a code segment that detects misregistration of successive steering frames using at least one of correlation block search, Doppler tissue velocity, an accelerometer, a motion sensor, feature tracking, cross correlation, and a sum of absolute differences.

26. A computer program in accordance with claim 23 further comprising a code segment that detects misregistration of successive steering frames using a compound image.

27. A computer program in accordance with claim 23 further comprising a code segment that combines a first number of steering frames when a first level of misregistration is detected, and combines a second number of steering frames when a second level of misregistration is detected, the first number of steering frames being greater than the second number of steering frames, and wherein the second level of misregistration is associated with a greater level of array transducer motion than the first level of misregistration.

28. A computer program in accordance with claim 22 further comprising a code segment that combines a plurality of steering frames into a compound image such that the number of steering frames combined is based on the detected array transducer motion.

29. A computer program in accordance with claim 22 further comprising a code segment that combines a plurality of steering frames into a compound image using a weighted average of the steering frames such that a weighting on the broadside steered frame is proportional to the detected motion.

30. A computer program in accordance with claim 22 further comprising a code segment that combines a plurality of steering frames into a compound image such that the number of steering frames combined is based on the detected array transducer motion using a compound image.

31. A computer program in accordance with claim 22 further comprising a code segment that transmits the plurality of ultrasound waves into the volume at a second rate based on the detected array transducer motion.

* * * * *